(12) United States Patent
Pihl et al.

(10) Patent No.: US 8,057,754 B2
(45) Date of Patent: Nov. 15, 2011

(54) APPARATUS AND METHOD FOR TIP ALIGNMENT IN MULTIWELL PLATES

(75) Inventors: Johan Pihl, Olofstorp (SE); Mattias Karlsson, Onsala (SE)

(73) Assignee: Cellectricon AB, Gothenburg (SE)

( * ) Notice: Subject to any disclaimer, the term of this patent is extended or adjusted under 35 U.S.C. 154(b) by 98 days.

(21) Appl. No.: 12/401,208

(22) Filed: Mar. 10, 2009

(65) Prior Publication Data

US 2009/0286297 A1    Nov. 19, 2009

Related U.S. Application Data

(60) Provisional application No. 61/069,229, filed on Mar. 12, 2008.

(51) Int. Cl.
*G01N 21/75* (2006.01)
*G01N 33/53* (2006.01)

(52) U.S. Cl. .................................... 422/407; 436/809

(58) Field of Classification Search ................. 422/407; 436/809
See application file for complete search history.

(56) References Cited

U.S. PATENT DOCUMENTS

| 4,493,815 | A |   | 1/1985 | Fernwood et al. |
| 5,424,213 | A | * | 6/1995 | Mougin ........................ 436/63 |
| 5,770,157 | A | * | 6/1998 | Cargill et al. ................ 506/40 |
| 6,495,369 | B1 | * | 12/2002 | Kercso et al. ................ 436/47 |
| 2002/0189374 | A1 | * | 12/2002 | DeSilets et al. ............ 73/864.51 |

FOREIGN PATENT DOCUMENTS

WO          9102073 A1     2/1991

* cited by examiner

*Primary Examiner* — Lore Jarrett

(74) *Attorney, Agent, or Firm* — Edwards Angell Palmer & Dodge LLP; David G. Conlin; Mark D. Russett

(57) ABSTRACT

Apparatuses and methods of aligning at least one tip of a tip manifold with a plurality of wells of a multiwell plate. The tip manifold includes a plate, at least one tip depending from the plate, a first tip alignment pin depending from the plate, and a second tip alignment pin depending from the plate. The second tip alignment pin opposes the first tip alignment pin. The multiwell plate includes a body defining a plurality of non-porous wells for holding biological material, a first alignment hole, and a second alignment hole. The second alignment hole opposes the first alignment hole.

6 Claims, 20 Drawing Sheets

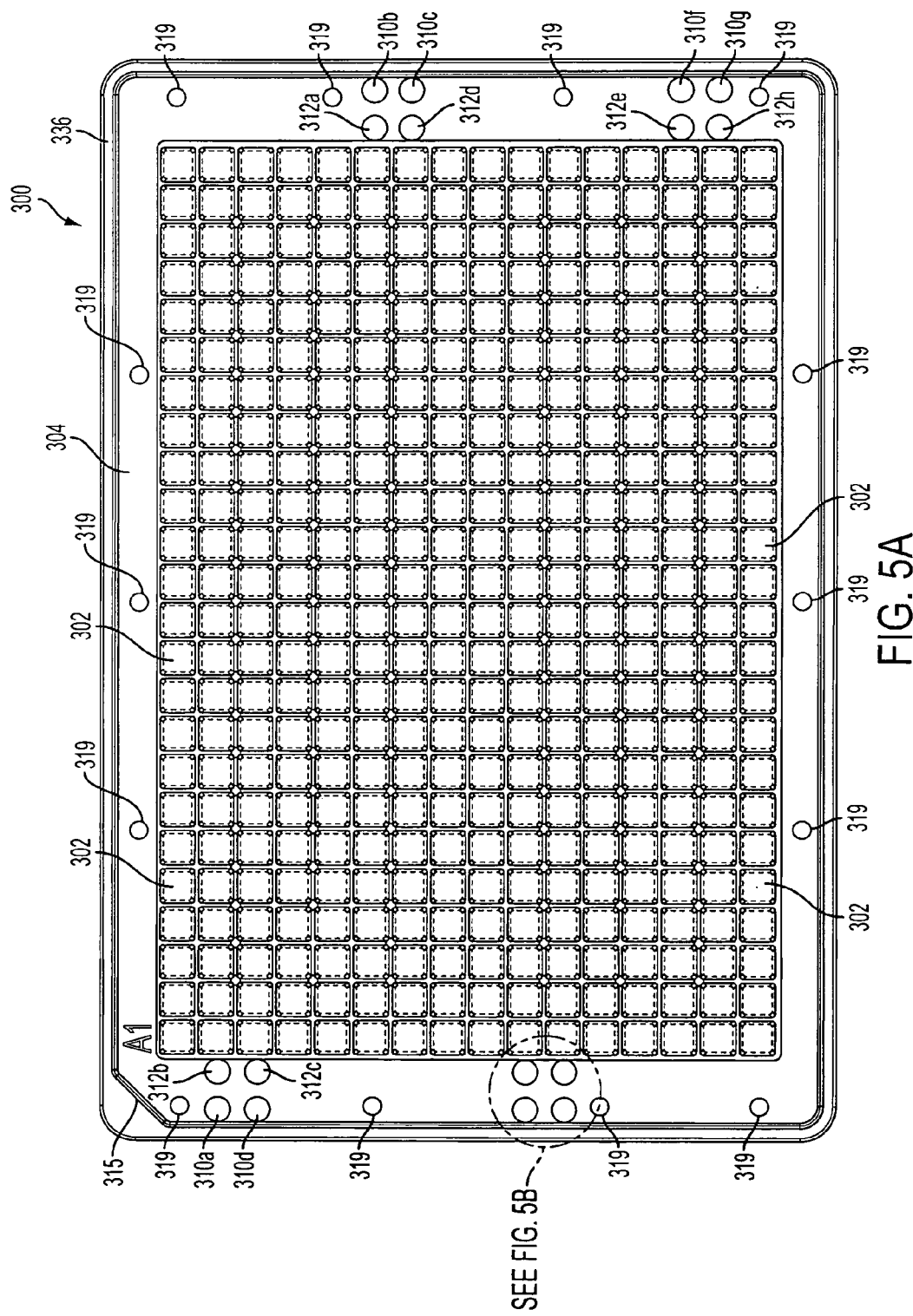

APPARATUS AND METHOD FOR TIP ALIGNMENT IN MULTIWELL PLATES

CROSS-REFERENCE TO RELATED APPLICATION

This application claims priority to U.S. Provisional Patent Application No. 61/069,229 filed Mar. 12, 2008 and U.S. Design Pat. Application No. 29/301,698 filed Mar. 12, 2008, each of which is incorporated herein by reference.

TECHNICAL FIELD

Automated screening and manipulation of biological materials in multiwell plates using tip assemblies.

BACKGROUND INFORMATION

Ribonucleic acid interference (RNAi) is one of the most exciting discoveries in biology in modern times and represents a revolution in the analysis of gene function. At present, genome-wide RNAi screens are becoming an increasingly important part in the process of target discovery. However, there is a lack of apparatuses and methods for the efficient tranfection of biologically relevant cell types at a sufficient throughput. For example, lipid-based methods can deliver in terms of throughput, but are unable to efficiently transfect most biologically relevant cell types. Methods based on conventional electroporation can transfect a wide range of primary and hard-to-transfect cell types, but are unable to do so at a price, efficiency and throughput required.

Electroporation is an increase the in the electrical conductivity and permeability of the cell membrane caused by an externally applied electrical field. In molecular biology, electroporation is used to introduce substances into a cell. For example, a nucleic acid can be introduced into a cell to change the cell's function. Electroporation is generally useful for introducing nucleic acids or other chemical or physical entities into tissue culture cells, including mammalian cells as well as to targeted organs in the living body. Electroporation applications include tumor treatment, gene therapy, cell-based therapy, and drug discovery.

In traditional electroporation techniques, electroporators create an electric current and pass it through a cell solution in a cuvette containing e.g. two metal electrodes on its sides. The cell suspension contained in the cuvette is mixed with a plasmid to be introduced into the cells. The cuvette is inserted into an electroporator, which applies a voltage (for example, 240 volts) to the electrodes and creates an electric field in the cell solution allowing the plasmid to enter the cell. After the cell solution is electroporated, the cells have to be handled carefully until they have had a chance to divide producing new cells that contain reproduced plasmids.

In many current electroporation practices, cells are detached from the cell culture vessel, placed in suspension, and transferred to cuvettes for electroporation as described above. This process is labor intensive and limits throughput and effectiveness. In addition, the electroporation step itself may cause significant stress to the cells and in combination with elaborate handling of cells such as scraping, digestion, transfer, pipetting and the like. As a result, high rates of cell morbidity and mortality are often observed.

SUMMARY

The purpose and advantages of the present invention will be set forth in, and become apparent from the description that follows. Additional advantages of the invention will be realized and attained by the apparatuses and methods particularly pointed out in the written description and claims hereof, as well as from the drawings. The various embodiments of the present invention provide a tip manifold and multiwell plate alignment apparatus, and methods in which the tips of the tip manifold can be aligned, lowered, and placed in close proximity to the surface of adherent cells cultured on the floor of a well in a multiwell plate. In electroporation applications, the subject technology can focus the electric field between the bottom of the well and a hollow tip electrode. In this way, the adherent (immobilized) cells are electroporated directly in their native state.

Another important advantage of the invention is that the alignment apparatus, and method facilitates high throughput screening, and is scalable to handle a high number of investigations to enable genome-wide RNAi screening on biologically relevant cell types. Other high throughput/high scale applications include cDNA screening, intracellular target characterization, biological systems interrogations of signalling pathways, and administration of intracellular drugs. Furthermore, the apparatuses of the various embodiments of the invention can be relatively easy and inexpensive to manufacture.

To achieve these and other advantages in accordance with the purpose of the invention, as embodied herein, the invention includes a method of aligning at least one tip of a tip manifold with a well(s) of a multiwell plate. The method includes providing at least one alignment hole. A preferred method has two alignment holes spaced apart a sufficient distance to allow sufficient angular accuracy. For example, the two alignment holes may be formed on opposite sides of the multiwell plate. The method further includes the step of providing at least one alignment pin positioned to align with the at least one alignment hole. The method further includes the steps of guiding the at least one tip into at least one of the plurality of wells by inserting the at least one alignment pin into at least one of the alignment holes. It is envisioned that the number, size and placement of the alignment holes/pins is flexible in view of serving the purpose of linearization of the tip axis with the wells.

In accordance with a further aspect of the invention, the at least one tip is an electroporation tip.

In accordance with another aspect of the invention, the at least one tip is a plurality equal to the number of wells in a multiwell plate.

In accordance with a further aspect of the invention, the at least one tip is a plurality equal to a portion of a number of wells in a multiwell plate.

In accordance with another aspect of the invention, the at least one tip is a plurality of a number of tips and the plurality of wells is a number of wells, wherein the number of wells is a multiple of the number of tips. Preferable, the method further includes repeating the step of guiding, wherein the total number of times the step of guiding is performed is at most equal to the multiple of the number of wells to the number of tips, such that plurality of tips is inserted into all or a portion of the plurality of wells.

The invention also provides a multiwell plate for accepting at least one tip of a tip manifold. The multiwell plate includes a body defining a plurality of wells for holding biological material, a first alignment hole, and a second alignment hole, wherein the second alignment hole opposes the first alignment hole. Generally, the first and second alignment holes are formed asymmetrically on the multiwell plate. Preferably, the wells of the multi-well plate are non-porous.

In accordance with a further aspect of the invention, the multiwell plate further forms a first alignment slot and a second alignment slot. The first and second alignment slots can be formed adjacent to the first and second alignment holes, respectively.

In still a further aspect of the invention, the body has a rectangular shape. The first alignment hole and the first alignment slot can be formed on a first short side of the body, and the second alignment hole and the second alignment slot can be formed on a second short side of the body. Preferably the body has a perimeter, the first alignment slot is formed closer to the perimeter than the first alignment hole, and the second alignment slot is formed closer to the perimeter than the second alignment hole.

In still a further aspect of the invention, the alignment holes and the alignment slots are formed as circles with a diameter within an exemplary range of 0.2 and 10.0 millimeters, each of the alignment slots has a slot center point formed within the alignment slot's center, each of the alignment holes has a hole center point formed within the alignment hole's center, and each of the slot center points is formed a distance of between an exemplary range of 0.2 and 10.0 millimeters or more from each of the adjacent hole center points.

In accordance with a further aspect of the invention, the body is fabricated from a material selected from the group consisting of: metal, ceramic, plastic, rubber, glass, and combinations thereof. The plurality of wells may be 6, 12, 24, 48, 96, 384, 1536, or 3456 wells.

The invention also provides an apparatus which includes a multiwell plate. The multiwell plate includes a body defining a plurality of wells for holding biological material, at least one alignment hole. In one embodiment, a second alignment hole opposes a first alignment hole. The apparatus includes a table and a robotic member for aligning the multiwell plate disposed on the table with a tip manifold. Preferably, the tip manifold comprises at least one tip, and the robotic member further aligns the multiwell plate perpendicularly with respect to the plane of the table.

In accordance with a further embodiment of the invention, the multiwell plate further forms at least one alignment slot. Preferably, the at least one alignment slot is a first and second alignment slot to secure a position of the multiwell plate on the table.

The invention also provides an apparatus including a tip manifold. The tip manifold includes a plate, at least one tip depending from the plate, at least one tip alignment pin depending from the plate. A second tip alignment pin may oppose a first tip alignment pin.

In accordance with a further embodiment of the invention, the at least one tip comprises electrodes, light guides, disposable plastic tips for dispensing liquids and the like.

In accordance with another embodiment of the invention, the tip manifold is an electroporation tip manifold.

In accordance with a further embodiment of the invention, the apparatus further includes a multiwell plate. The multiwell plate includes a body defining a plurality of wells (e.g., non-porous wells) for holding biological material, a first alignment hole, and a second alignment hole. Preferably, the second alignment hole opposes the first alignment hole. In still a further embodiment of the invention, the at least one tip consists of at least one electrolyte-filled capillary electrode having a non-conducting capillary wall, wherein the at least one tip is lowered into the respective wells. Each of the wells has a surface defined by the bottom of the well, and the at least one tip can be lowered to a predetermined distance from the surface of the respective well. In one embodiment, the predetermined distance is 75 micrometers but variable from one or even several millimeters down to micrometers or even submicrometers is contemplated.

In accordance with a further embodiment of the invention, the alignment holes form a circle, and the alignment pins have a circular cross-section and are designed to fit snuggly into the alignment holes. When a single alignment hole is used together with a single alignment pin, the pin and receiving hole has a geometric form such that alignment in x-y direction is achieved. For example, the cross section of the pin can be star-shaped, cross-shaped, or triangular with receiving holes being star-shaped, cross-shaped, and triangular, respectively. Preferably, the first and second alignment pins have a pin length and the at least one tip has a tip length. The pin length is longer than the tip length, and the tip manifold is configured such that the alignment pins insert into the respective alignment holes before the at least one tip inserts into the respective wells for precision alignment.

In accordance with another embodiment of the invention, the alignment pin(s) has a rounded end facing the alignment hole(s) such that as the alignment pin(s) is inserted into the alignment hole(s), the multiwell plate slides laterally until the alignment pin(s) inserts into the alignment hole(s).

In still a further embodiment of the invention, the tips are spring-loaded to allow vertical compliance when the tips contact the plate. The wells further define a bottom surface at the bottom of the wells, and the biased body is normally extended distally by a force from the spring but moves proximally to provide compliance in a direction perpendicular to the plane of the multiwell plate body when inserted into the wells and contacted with the bottom surface. Preferably, the tips are electroporation tips.

In accordance with a further embodiment of the invention, a robotic member is coupled to the tip manifold. The robotic member facilitates the alignment of the alignment pins with the alignment holes and lowers the at least one tip of the tip manifold into the respective wells.

In accordance with another embodiment of the invention, the at least one tip is an array of a number of tips, the tips of the array arranged in at least one row comprising at least one tip. The number of tips may equal the number of wells of the multi-well plate. The number of wells can be, but are not limited to, 6, 12, 24, 48, 96, 384, 1536, or 3456 wells.

In still a further embodiment of the invention, a number of wells is equal to a multiple of the number of tips such that the at least one tip is configured to align with a portion of the respective wells and insert into the portion of respective wells.

In accordance with another embodiment of the invention, the tips are arranged in a matrix of at least one tip comprising a number of tips. The plurality of wells forms a matrix of wells including a number of wells. The number of wells is a multiple of the number of tips. The matrix of wells is divided into at least one group of wells. The total number of alignment holes may be equal to the multiple of tips to wells. Half of the alignment holes may be formed on one of the opposing sides of the multiwell plate with half of the alignment holes may be formed on the other of the opposing sides of the multiwell plate. The alignment pins are configured to align with respective alignment holes, and to insert into the holes a number of dip times equal to the multiple of wells to tips.

It is to be understood that both the foregoing general description and the following description are exemplary and are intended to provide further explanation of the invention claimed.

The accompanying figures, which are incorporated in, and constitute part of this specification, are included to illustrate and provide a further understanding of the apparatus and method of the invention. Together with the description, the drawings serve to explain the principles of the invention. All relative descriptions herein such as left, right, up, down, forward, and backward are with reference to the Figures, and not meant in a limiting sense.

BRIEF DESCRIPTION OF THE DRAWINGS

The following description, given by way of example, but not intended to limit the invention to the specific embodiments described, may be understood in conjunction with the accompanying drawings, incorporated herein by reference. Various preferred embodiments of the present invention will be described by way of non-limiting examples and with reference to the accompanying drawings in which:

FIG. 5A is a detailed top or plan view of the multiwell plate of the embodiment of the invention shown in FIG. 1;

DESCRIPTION

I. Definitions

Figure 1:
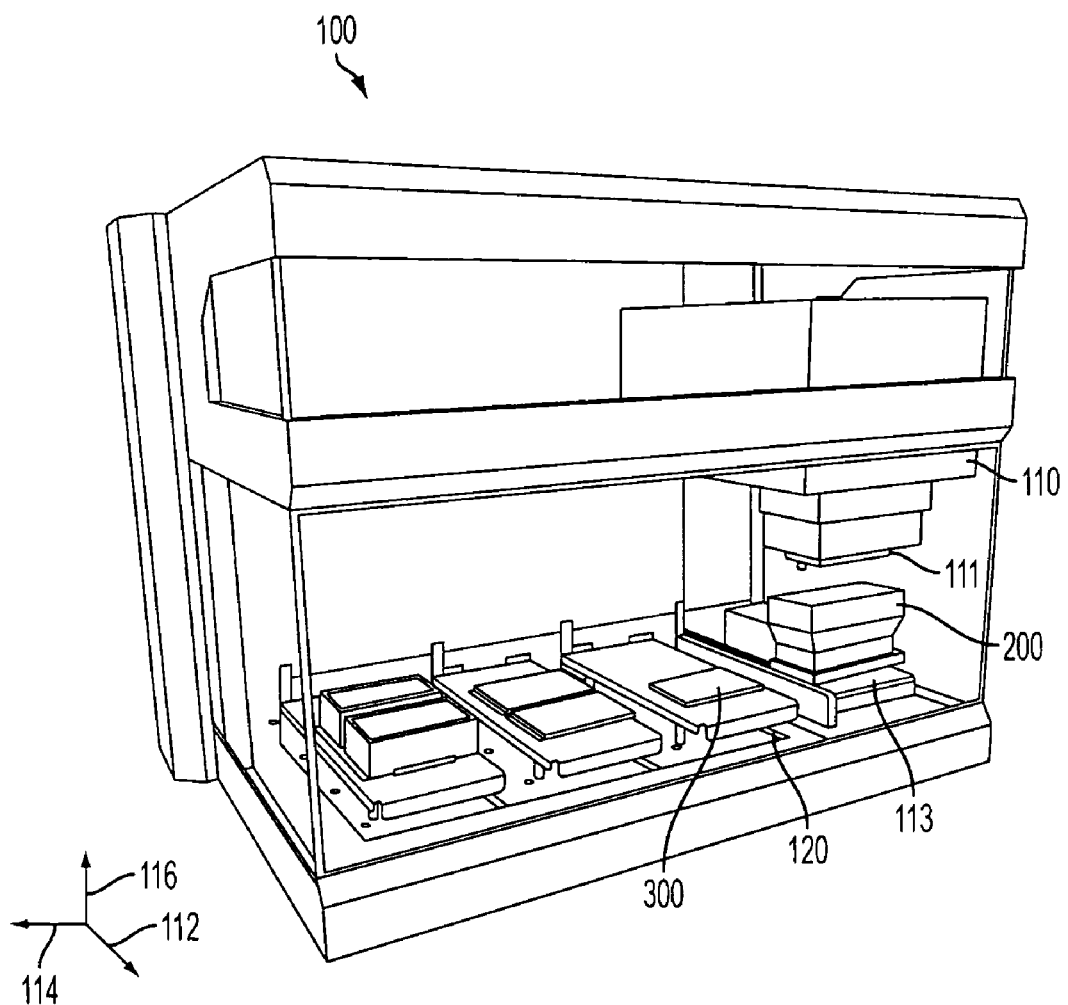
FIG. 1 illustrates a system which can practice the invention.

The term "multiwell plate" is meant to include a structure defining any number of wells for holding biological, chemical, or physical materials for screening processes.

The term "non-porous" is meant to describe the characteristics of a body material for holding of materials disposed within a well without leakage of the materials through the body material. For example, a plastic body material can be described as non-porous because it can hold a biological material without the biological material leaking through the plastic body material.

The term "tip manifold" is meant to include a structure for holding any number of tips which are structures for holding and/or dispensing biological materials including liquids in the wells and/or electroporating a biological sample. The tips of the tip manifold are configured and arranged to generally co-align with the wells.

The term "electroporation" is meant to include the application of a significant voltage thereby permeabilizing a cell bilayer membrane such as the plasma membrane caused by the applied electrical field. Electroporation can, among other applications, be used in molecular biology as a way of introducing some substance (e.g., DNA, RNA, siRNA, small molecules, peptides, proteins, antibodies) into a cell, such as loading it with a molecular probe, a drug that can change the cell's function, or a nucleic acid.

The term "biological material" is meant to include any material formed or recently formed of living matter. For example, a biological material can include cell tissue, plant matter, compounds which occur in living cells, processed living materials, materials capable of living, and organically formed materials such as soils and other organic matter.

The term "screening" is meant to include investigation of a great number of something (for instance, biological material samples) looking for those with a particular problem or feature. Screening can be conducted in a variety of fields in which the invention may be practiced including, but not limited to, pharmacology, medicine, etc. For example, in pharmacology, screening may be performed for the investigation of pharmacological activity during drug discovery (e.g., detecting a biological activity (e.g., cell proliferation) of a chemical compound on a cell).

The term "nucleic acid" is meant to include a macromolecule composed of nucleotide chains. For example, molecules can carry genetic information or form structures within cells. Common nucleic acids include deoxyribonucleic acid (DNA) and ribonucleic acid (RNA).

II. Systems and Methods

The automated screening and manipulation of biological materials in multiwell plates requires the positioning of tip assemblies with respect to the plate wells. For example, the system and method of the invention are well-suited for performing RNA interference (RNAi), and complementary DNA (cDNA) high-throughput screening transfections based on electroporation with electrolyte-filled capillaries (EFCs).

Multiwell plates of the invention can be used in a number of screening applications. One common application is to dispense liquids into the multiwell plates such that each well in the plate receives a controlled and predetermined amount of an agent. Examples of such agents include genetic materials, proteins, peptides, drugs, potentiators, bioactive compounds in general, inhibitors, and dyes. The dispensing of liquids into the multiwell plates can be performed with a pipette-tip manifold were each pipette tip addresses a given well in the well plate.

For example, all 96 wells in a 96-well multiwell plate can simultaneously receive up to 96 different solutions from the 96 different pipette tips in the tip manifold such that each addition of liquid ends up in the respective well. The tips can be aligned in arrays in the tip manifold such that the placement of the individual tips (for example, the distance between each of the tips) corresponds to the placement of the wells in the multiwell plate.

The wells can contain, for example, cells grown on the bottom, cells in suspension, or they can contain a reagent or a chemical species such as an enzyme. The solution added to the wells can contain a drug such that when the drug is added to the wells at different concentrations, information on binding affinity for the cells can be obtained. The solution can contain a substrate such that when the substrate is added to the wells containing an enzyme, information on rates of reaction can be obtained.

Multiwell plates of the invention can be used for many robotic screening applications including, capillary electroporation, and some electrochemical, and optical applications where the exact placement of the tip relative to, for example, a layer of cells grown on the bottom of each well is critical to the outcome of the experiment.

FIG. 1 shows a system 100 in which the automated screening and manipulation of biological material can be practiced according to the invention. The system 100 may include an enclosed, temperature and humidity controlled, filtered space to promote favorable parameters for the methods described herein. The system 100 includes a tip manifold 200 and multiwell plate 300. A robotic member 110 is for general positioning of the tip manifold 200. The robotic member 110 has a lower end 111 adapted and configured to selectively couple to various tip manifolds. When not in use, the tip manifold 200 may be placed in a park station 113.

The multiwell plate 300 can be disposed on a table 120. The tip manifold 200, by being attached to the robotic member 110, can be moved in various directions with respect to the multiwell plate 300. For example with respect to the axis 112, 114, 116 shown in FIG. 1, the tip manifold 200 can move forward and backward along axis 112 in the plane parallel to the plane of the multiwell plate, left and right along axis 114 in the plane parallel to the plane of the multiwell plate, and up and down along axis 116 in the plane perpendicular to the plane of the multiwell plate 200 or table 120. Alternatively, the robotic member 110 can be attached to the multiwell plate 200 or table 120 for general positioning with respect to the tip manifold 200.

Figure 2:
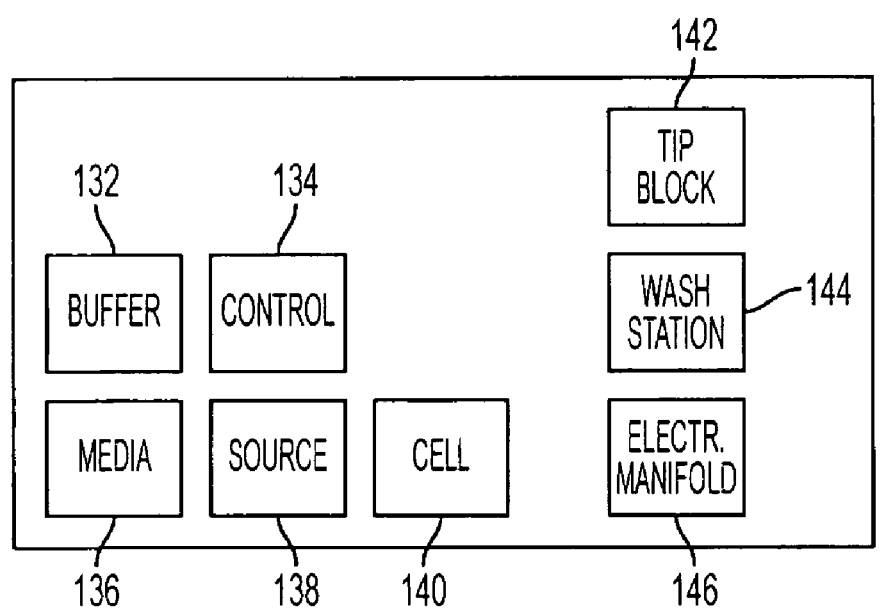
FIG. 2 is a top somewhat schematic view of the environment illustrated in FIG. 1.

Referring now to FIG. 2, a somewhat schematic top view of the system 100 is shown. The system 100 includes stations 132, 134, 136, 138, 140 for holding various components and materials for screening. For example, the stations 132, 134, 136, 138, 140 can hold buffer compounds 132, control compounds 134, various media 136, sources 138, and cell materials 140. Other stations 142, 144, 146 can hold tip blocks 142, wash stations 144, and tip manifolds 146. The robotic member 110 attached to the tip manifold 200 can be manipulated to combine one or more materials for screening, for example, a buffer 132, a control 134, and a cell culture 140. The robotic member 110 can be programmed to pick up a tip block 142 and wash the tips in the wash station 144 as needed for the screening processes.

Figure 3:
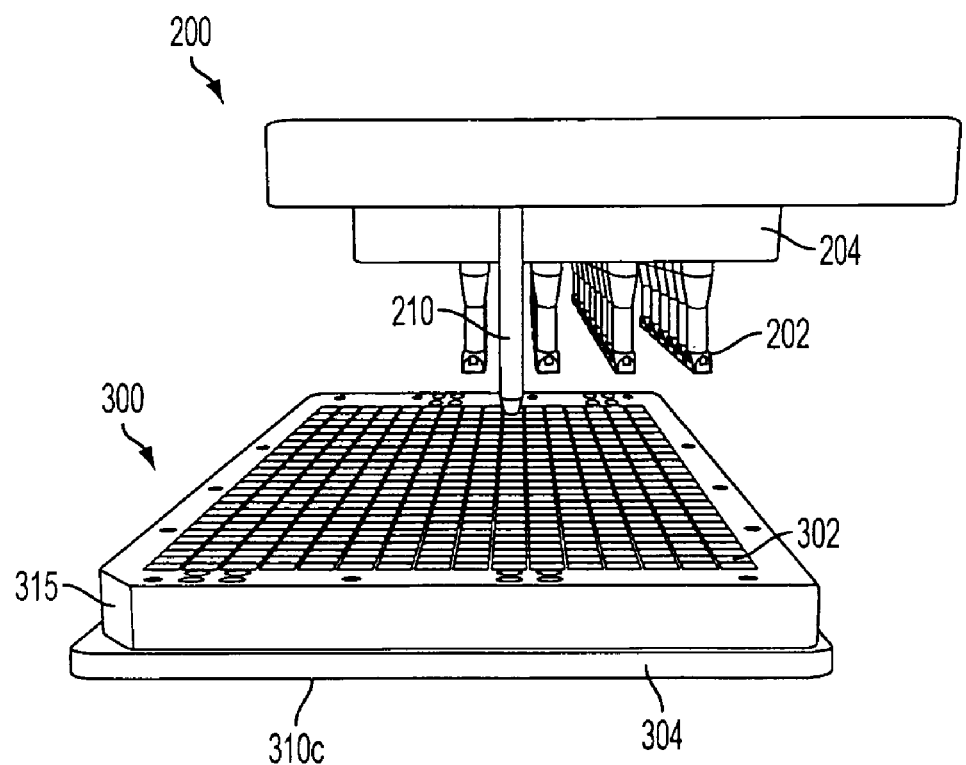
FIG. 3 illustrates an embodiment of the subject technology showing the electroporation tip manifold including alignment pins and electroporation tips, and the multiwell plate including eight pairs of alignment holes and slots.
Figure 4:
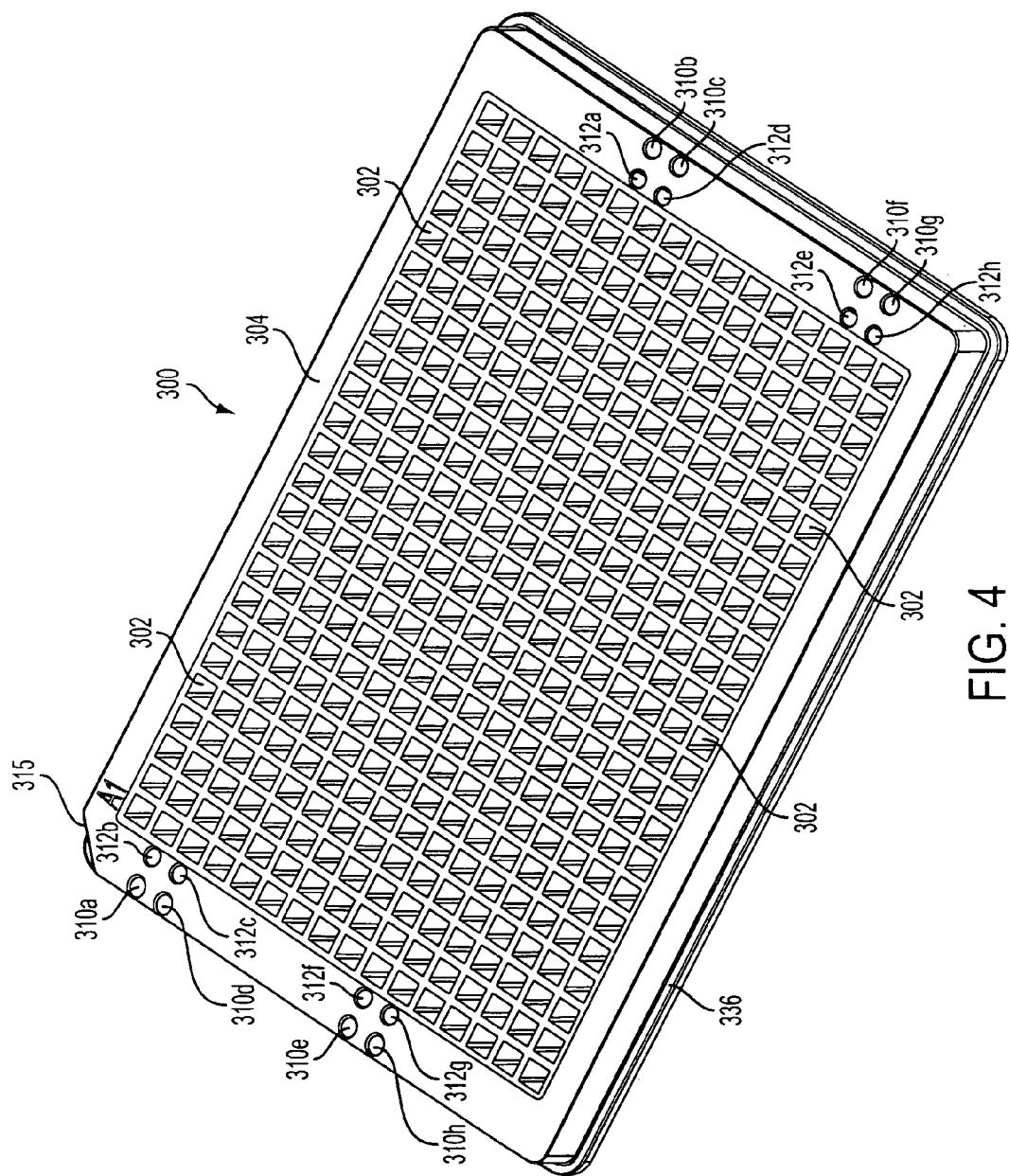
FIG. 4 illustrates a perspective view of the multiwell plate of the embodiment of the subject technology shown in FIG. 1.
Figure 5B:
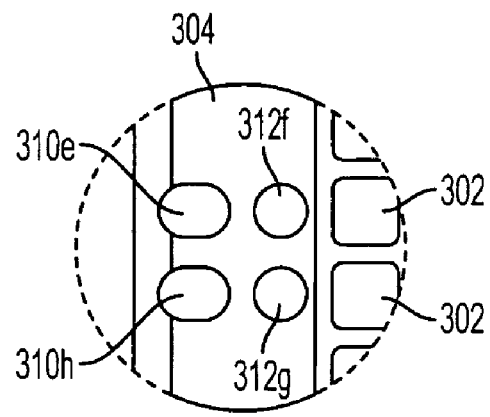
FIG. 5B is a detailed view of a portion in circle B showing some alignment holes and alignment slots shown in FIG. 5A.
Figure 5C:
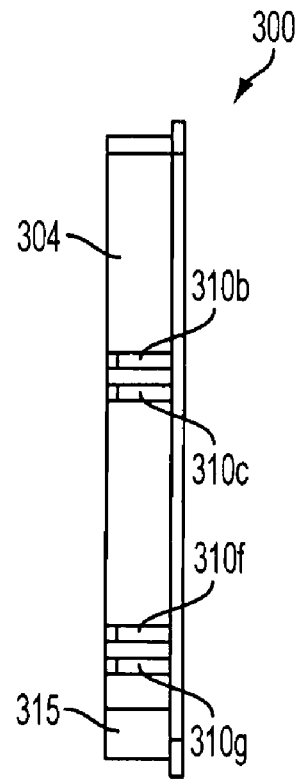
FIG. 5C is a side view of the multiwell plate shown in FIG. 5A.

Referring to FIG. 3, the invention provides a multiwell plate 300 for accepting at a plurality of tips 202 of the tip manifold 200. The multiwell plate 300, also shown in FIGS. 4, 5A, 5B, and 5C, includes a body 304 defining a plurality of non-porous wells 302 for holding biological material. The biological material may include cells grown at the bottom of the wells 302 or cells in suspension.

The multiwell plate 300 may have one or more banking surfaces 315 for the initial positioning of the multiwell plate 300 on the table 120. In order to properly engage the tips 202 in the wells 302, the tip manifold 200 has alignment pins 210, 212 that first engage alignment apertures 310a-h, 312a-h in the multiwell plate 300.

In the multiwell plate 300, there are eight pairs of alignment apertures 310a-h, 312a-h. In each pair, an alignment slot 310a-h opposes a respective circular alignment hole 312a-h. The pairs of alignment slots and holes 310a-h, 312a-h can be formed asymmetrically on the multiwell plate 300. For example, the alignment holes 310a, 312a can be formed on opposite sides of the body 304. In the alternative, the pairs of alignment apertures can be formed on adjacent sides of the body 304, close to each other or in any configuration appropriate for the screening process that allows accurate alignment with the tip manifold 200. In the configuration shown, the alignment apertures are set in four groups, each group having two slots 310 near the periphery and two holes 312 inwardly located from the adjacent slots 310.

The body 304 of the multiwell plate 300 may define more or less than sixteen alignment apertures 310, 312, for example, one, two, three, four, five, etc., depending on the configuration of the multiwell plate 300, the tip manifold 200, and the needs of the screening application.

As shown in FIGS. 3, 4, 5A-C, and 6, to the multiwell plate 300 has sixteen alignment apertures and the tip manifold 200 has a 4-12 array of tips. Thus, to cover 384 wells using 48 tips of a tip manifold 200, the body 304 of the multiwell plate 300 can be configured to define sixteen apertures 310a-h, 312a-h (e.g., eight pairs) for a total of eight separate dips of the tip manifold 200. As such, each dip would utilize a different pair of alignment apertures 310, 312. The tip manifold 200 is preferably an electroporation tip manifold having a four by twelve array of tips 202 with a 9 mm pitch as opposed to a 4.5 mm pitch of the wells 302 in the multiwell plate 300.

In accordance with a further aspect of the invention, the multiwell plate 300 may have features on a bottom side or use the alignment apertures 310, 312 fully, partially or temporarily to set the multiwell plate 300 on the table 120. Additionally, the banking surface 315 or another part of the multiwell plate 300 could simply abut a complementary surface on the table 120 to accomplish a rough positioning of the multiwell plate 300. On a bottom side, the multiwell plate 300 may have 3 points (not shown) to interact with 3 points such as a flat area, a notched area and a semi-dome to locate the multiwell plate 300 in six axis (axis 112, 114, 116 and rotation about same) in a highly precise manner. The bottom side preferably also includes supporting beams to add structural stability. One version has a plurality of long supporting beams running parallel to the edges and a plurality of shorter supporting beams running perpendicular to the edges. The number and configuration of the supporting beams can be varied as desired.

Preferably, the alignment apertures 310, 312 can be formed in other parts of the multiwell plate 300, for example, the corners of the multiwell plates. The multiwell plate 300 can further form three, four, or any number of alignment apertures of varying sizes and shapes depending on the needs of the application. For example, larger mechanical components may require more than two slots for added stability. For another example, one or more slots may be "+" or "−" shaped so that only a single hole in combination with a "+" or "−" alignment pin can locate the multiwell plate 300 laterally and rotationally. Many other shape alignment pin and hole combinations can provide 3 degree adjustment (axis 112, axis 114 and rotation about axis 116 with respect to FIG. 1) such as a triangle, keyhole and like shapes.

As best seen in FIG. 5A, the body 304 has a rectangular shape. The alignment apertures 310, 312 can be formed on the first short sides of the body 304 with the alignment slots 310 formed closer to the perimeter 336 than the alignment holes 312. The body 304 is not limited to a rectangular shape, and can have a square, circular, polygonal, oval, or any other appropriate shape, or combinations thereof, for the screening application. Also, the alignment slots 310 need not be formed closer to the perimeter, for example, the slots 310 could be formed further from the perimeter than the holes 312, for example, in a portion of the body 310 proximal to the center of the body 304.

The alignment apertures 310, 312 may be formed in separate sections of the multiwell plate body 304. Additionally, the table 120 may have upstanding ridges or a like structure to initially guide placement of the multiwell plate 300 and serve to accept the alignment pins 210. Accordingly, the multiwell plate 300 would not require alignment apertures. In still another embodiment, the table 120 may include moving pins that initially align the multiwell plate 300 via the alignment apertures 310, 312, then the moving pins are retracted to allow using the alignment apertures 310, 312 for alignment to the tip manifold 200.

In still a further aspect of the invention, the alignment apertures 310, 312 are both formed as circles. Also, each of the alignment apertures 310, 312 has a hole center point formed. The alignment holes 310, 312 can be formed as other shapes, for example, squares and shapes with more than four sides, for example, hexagons. Furthermore, the diameters of the alignment holes and distances between the center points 325 of the alignment holes can vary depending on the needs of the screening application. In one embodiment, the body 304 is made be injection molding. During such manufacturing, ejector pins (not shown) may be used to remove the body 304 from the mold (not shown). As a result, ejector pin impressions may be appear on the body 304 as a plurality of circles 319. The circles 319 would not be through holes or even recessed.

The body 304 may be fabricated from: metal, ceramic, plastic, rubber, glass, and the like as well as combinations thereof. The number of wells comprises 6, 12, 24, 48, 96, 384, 1536 or 3456 wells. The number of wells can be an even or odd number.

Figure 6:
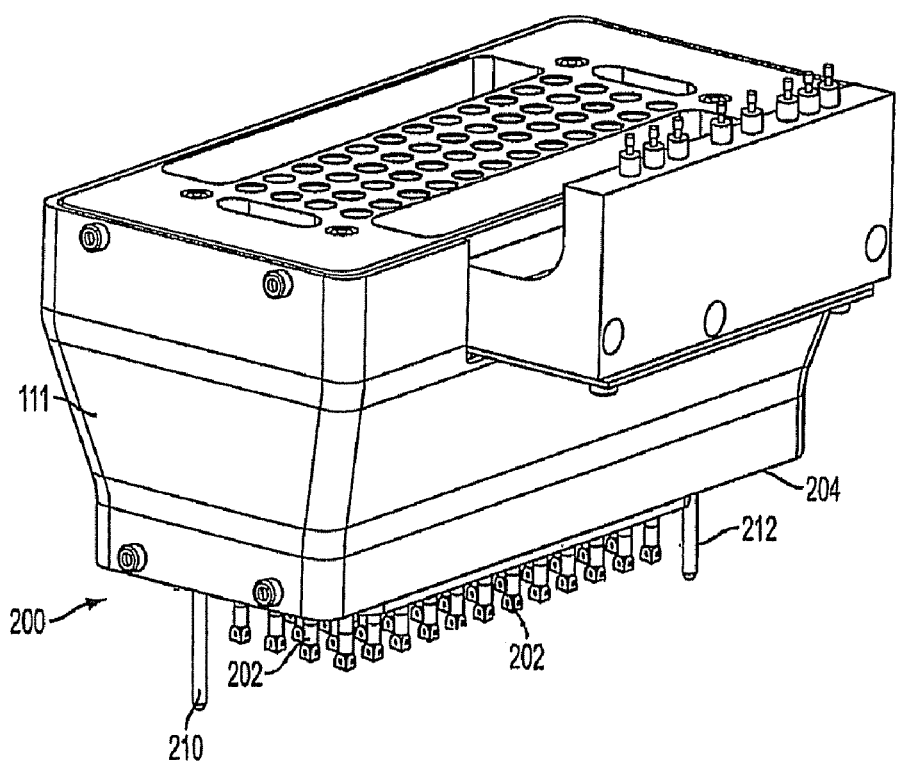
FIG. 6 is a perspective view of the electroporation tip manifold of the embodiment of the invention shown in FIG. 1.

The system 100 also includes a tip manifold 200, an embodiment of which is shown in FIG. 6. The tip manifold includes a plate 204 and a plurality of tips 202 which depend from the plate 204. First and second tip alignment pins 210, 212 also depend from the plate 204. The second tip alignment pin 212 opposes the first tip alignment pin 210 so that pairs of opposing alignment apertures 310, 312 can be utilized for alignment.

The tip 202 includes electrodes or light guides or dispensing tips such as disposable plastic pipette tips. The electrodes can be used for electroporation of the biological material and the tips can be electrolyte-filled capillaries or tips. The electrodes can also be solid e.g. cylindrical electrodes for measuring oxidative or reductive processes. The light guides can be used for exposing the biological material to light and the tips can be fiber optic lumens for channeling the light, or for measuring light emitted from the wells and/or the cells, e.g. fluorescence or luminescence. The disposable tips can be used for demanding applications for liquid addition or withdrawal where a high positional precision and cleanliness are required.

Figure 7A:
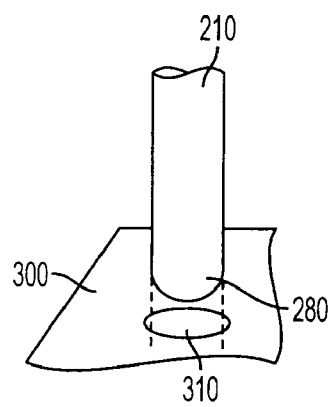
FIG. 7A illustrates an embodiment of the alignment pin of the tip manifold with a rounded end adjacent an alignment hole of the multiwell plate.
Figure 7B:
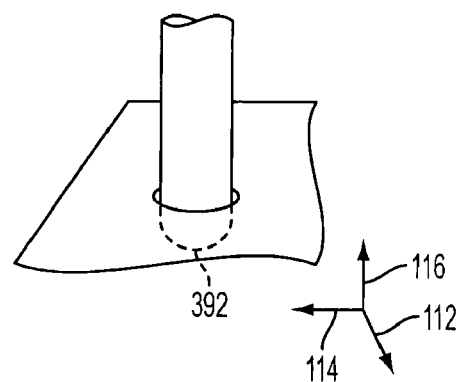
FIG. 7B illustrates the pin lowered into the alignment hole of FIG. 7A.

Referring now to FIGS. 7A and 7B, a sequence for aligning the tips 202 and the wells 302 is partially shown to illustrate the process. FIG. 7A, in particular, illustrates an alignment pin 210 of the tip manifold with a rounded end adjacent an alignment slot 310 of the multiwell plate 300. As noted above, the tip manifold 200 is selectively coupled to the robotic member 110. By moving along the axis 112, 114, 116, the robotic member 110 positions the alignment pins 210, 212 above respective alignment holes 310, 312. For simplicity, only pin 210 and alignment slot 310 are shown in FIGS. 7A and 7B.

The alignment pins 210, 212 have a rounded end 280 facing the alignment apertures 310, 312. The multiwell plate 300 can be disposed on the table 120 and although initially located, the multiwell plate 300 can be freely movable as noted above. The multiwell plate 300 is initially placed such that the alignment pins 210, 212 of the tip manifold 200 at least partially align with the alignment apertures 310, 312, but the final alignment of the multiwell plate 300 to the tip manifold 200 and, thereby, the tips 202 to the wells 302 is accomplished by inserting the alignment pins 210, 212 into a pair of alignment apertures 310, 312.

Referring now to FIG. 7B, the pin 210 is fully inserted in the alignment hole 310. The axis 112, 114, 116 of FIG. 1 have been reproduced for directional reference. To insert the pins 210, 212, the tip manifold 200 is lowered along axis 116 toward the multiwell plate 300. As the pins 210, 212 enter the alignment apertures 310, 312, the rounded ends 280 of the alignment pins 210, 212 force the multiwell plate 300 to move laterally in the horizontal plane defined by axis 112, 114. Because there are two alignment apertures 310, 312 being moved by two pins 210, 212, the multiwell plate 300 will also adjust in a rotational manner about axis 116, e.g., a three-axis adjustment. The tips 210, 212 are relatively longer and depend closer to the multiwell plate 300 so that alignment occurs prior to the tips 202 reaching the wells 302. In this way, all the tips 202 and wells 302 are positioned and aligned perfectly in preparation for insertion of the tips 202 into the wells 302. Alternatively, triangular pin and one triangular hole could be used for three-axis adjustment and the like. For another example, rotational alignment may be precluded if the multiwell plate is held in proper alignment by walls extending perpendicularly from the table 120 and contacting the multiwell plate 300 at the banking surface 315 or other location. Hence, only a lateral adjustment may be needed by insertion of a pin in a hole.

Figure 8:
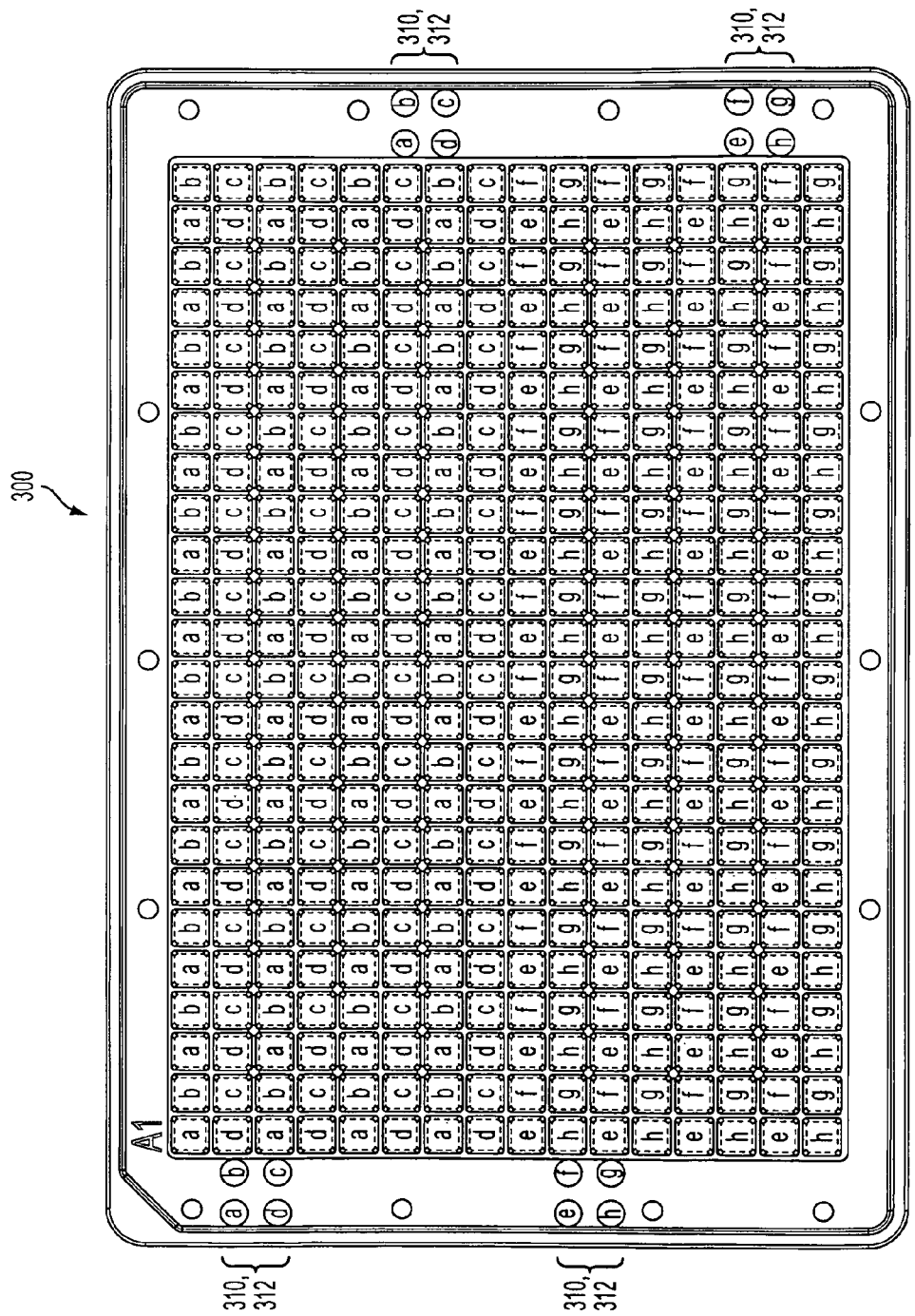
FIG. 8 illustrates one possible insertion sequence for covering a 384 multiwell plate with the 48 tip manifold shown in FIG. 1.

Referring now to FIG. 8, one possible insertion pattern for covering every well in a 384 multiwell plate 300 with the 48 tip manifold 200 shown in FIG. 1 is illustrated. The multiwell plate 300 has 384 wells 302 arranged in 16 rows of 24 wells/row. The tip manifold 200 has 4 rows of 12 tips/row spaced twice as far apart as the wells 302. Accordingly, it will take 8 aligned dips of the tip manifold 200 to access each well 302. Eight pairs of opposing alignment holes 310a-h, 312a-h are formed in the body 304 to orient the eight dips. The subject technology is not limited to this configuration, for example, the tip rows may be spaced every signal well row, every third well row, and every fourth well row, etc., based on the needs of the screening process.

In more detail, to accomplish the screening, the robotic member 110 moves the tip manifold 200 between the eight pairs of alignment hole 310a-h, 312a-h and, thereby inserts a tip 202 in every well 302. For example, when the pins 210, 212 of the tip manifold 200 are aligned into the alignment holes 310a, 312a as described above, the tips 202 are aligned and inserted into the wells 302 labeled with an "a". When the pins 210, 212 of the tip manifold 200 are aligned into the alignment holes 310b, 312b as described above, the tips 202 are aligned and inserted into the wells 302 labeled with a "b" and so on. After completing the fourth dip by aligning to the holes 310d, 312d, the robotic member 110 jumps down to the lower pairs of alignment holes 310e-h, 312e-h and continues. As can be seen, the robotic member 110 moves the tip manifold in the two-stage boustrophedonic pattern show in the wells 302 labeled a-h.

In the embodiment, the tips 202 have a 9 mm row pitch and a 9 mm column pitch, and the wells 302 have a 4.5 mm row pitch and a 4.5 mm column pitch. Thus, the tips 202 of the tip manifold 200 are arranged in rows spaced every other row of the well rows, and in columns spaced every other column of the well columns.

In one embodiment, the subject technology includes an apparatus including a multiwell plate 300. The multiwell plate includes a body 304 defining a plurality of non-porous wells 302 for holding biological material, a first alignment hole 310, and a second alignment hole 312, wherein the second alignment hole 312 opposes the first alignment hole 310. The apparatus includes a table 120 and a robotic member 110 for aligning the multiwell plate 300 disposed on the table 120 with a tip manifold 200. Preferably, the tip manifold 200 comprises at least one tip 202, and the robotic member 110 further aligns the multiwell plate vertically 116 (in the up/down direction) with respect to the plane of the table 120.

In accordance with a further embodiment of the invention, the multiwell plate further forms a pair of alignment holes 310, 312 that serve to secure a position of the multiwell plate 300 on the table 120 and align the tip manifold 200.

In one embodiment, the subject technology includes a method of aligning at least one tip 202 of a tip manifold 200 with a plurality of wells 302 of a multiwell plate 300. One method includes providing at least two alignment holes 310, 312, at least one of the alignment holes formed on one side of the multiwell plate 300, and at least one of the alignment holes formed on the opposite side of the multiwell plate 300. The method provides at least two alignment pins 210, 212, at least one of the alignment pins coupled to one side of the tip manifold 200, and at least one of the alignment pins coupled to the opposite side of the tip manifold 200. The method includes guiding the at least one tip 202 into at least one of the plurality of wells 302 by inserting the at least one alignment pin coupled to one side of the tip manifold into at least one of the alignment holes, and inserting the at least one alignment pin coupled to the opposite side of the tip manifold into at least one of the other alignment holes. In accordance with a further aspect of the invention, the at least one tip is an electroporation tip.

In accordance with another embodiment of the invention, the tip manifold 200 has an array of a number of tips 202. The tips 202 of the array are arranged in at least one row comprising at least one tip (see FIG. 6 having a four by twelve array of tips 202). The number of tips 202 may equal a number of wells 302. The plurality of wells 302 may include any number of wells such as 6, 12, 24, 48, 96, 384, 1536 or 3456 wells. In still a further embodiment of the invention, a number of wells is equal to a multiple of the number of tips such that the at least one tip is configured to align with a portion of the respective wells and insert into the portion of respective wells. Suitable electroporation tips and methods of use are known in the art. For example, the electroporation tips described in U.S. Pat. No. 6,521,430 and U.S. Publication Nos: 2005/0048651 and 2005/0026283, all of which are herein incorporated by reference in their entirety, can be adapted for use in the present apparatus.

Figure 9A:
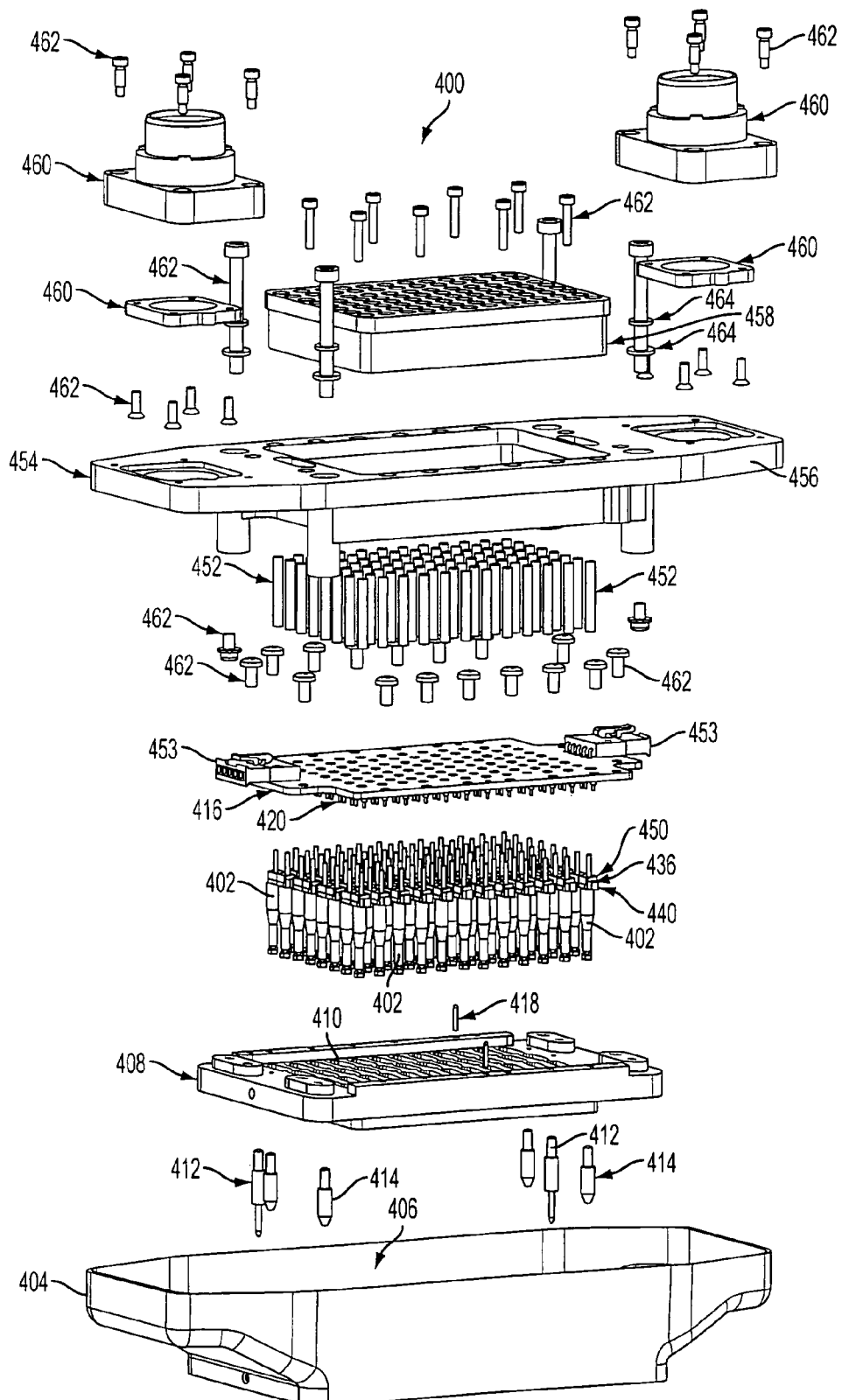
FIG. 9A is an exploded view of another electroporation tip manifold including alignment pins and ninety-six electroporation tips.
Figure 9B:
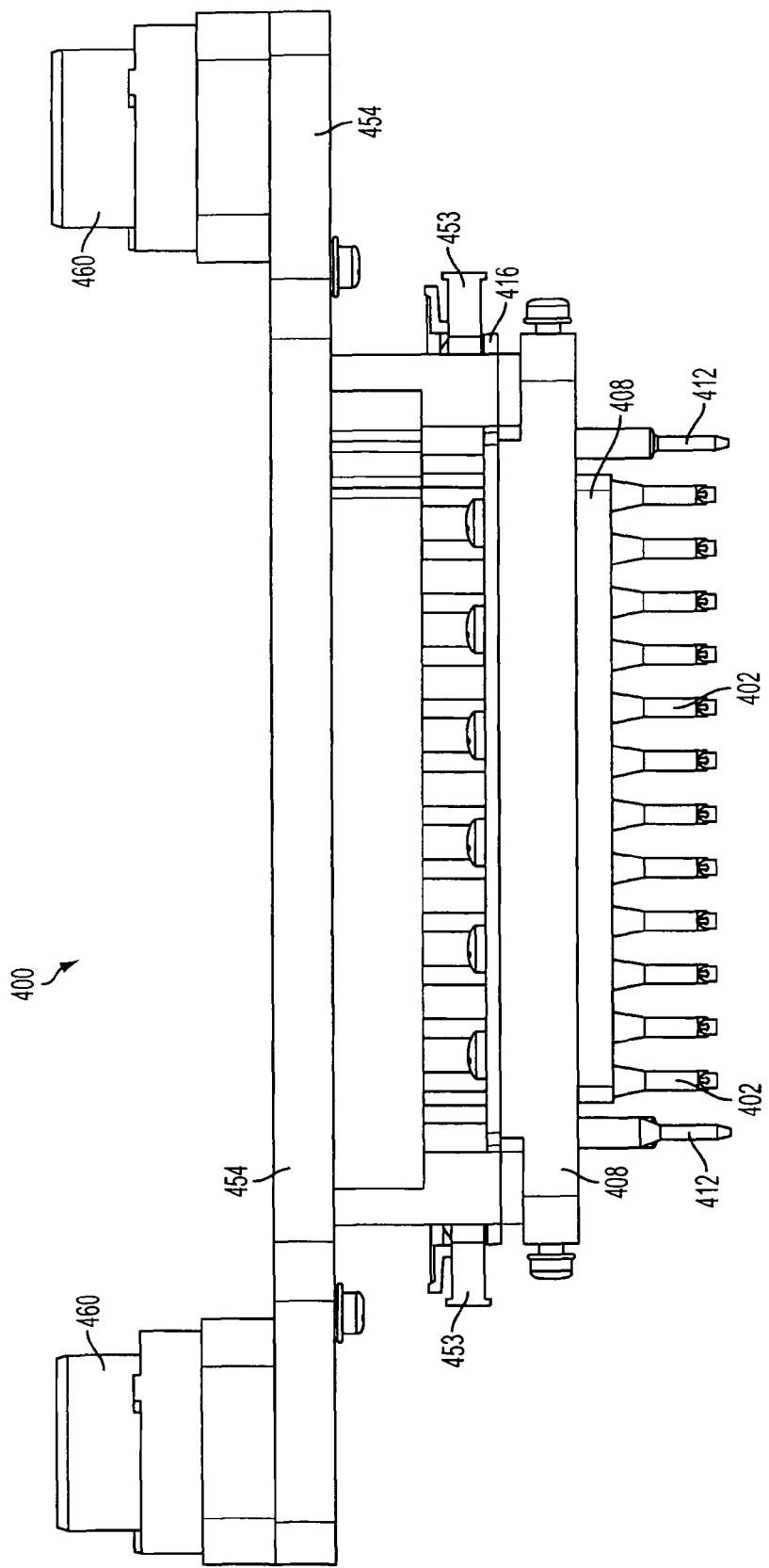
FIG. 9B is a front view of the electroporation tip manifold of FIG. 9A with the cover removed to show the components therein.
Figure 9C:
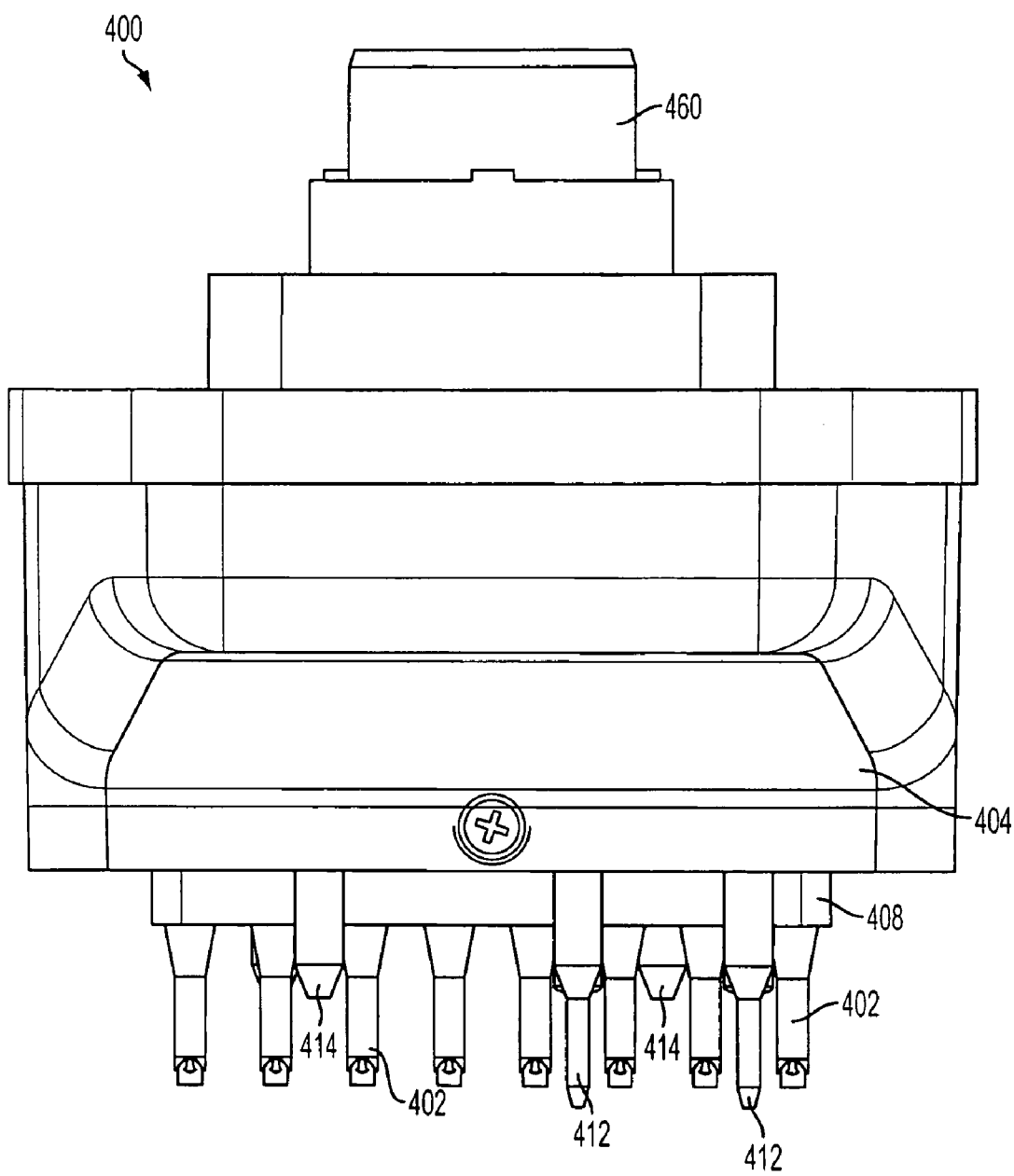
FIG. 9C is a side view of the electroporation tip manifold of FIG. 9A.
Figure 9D:
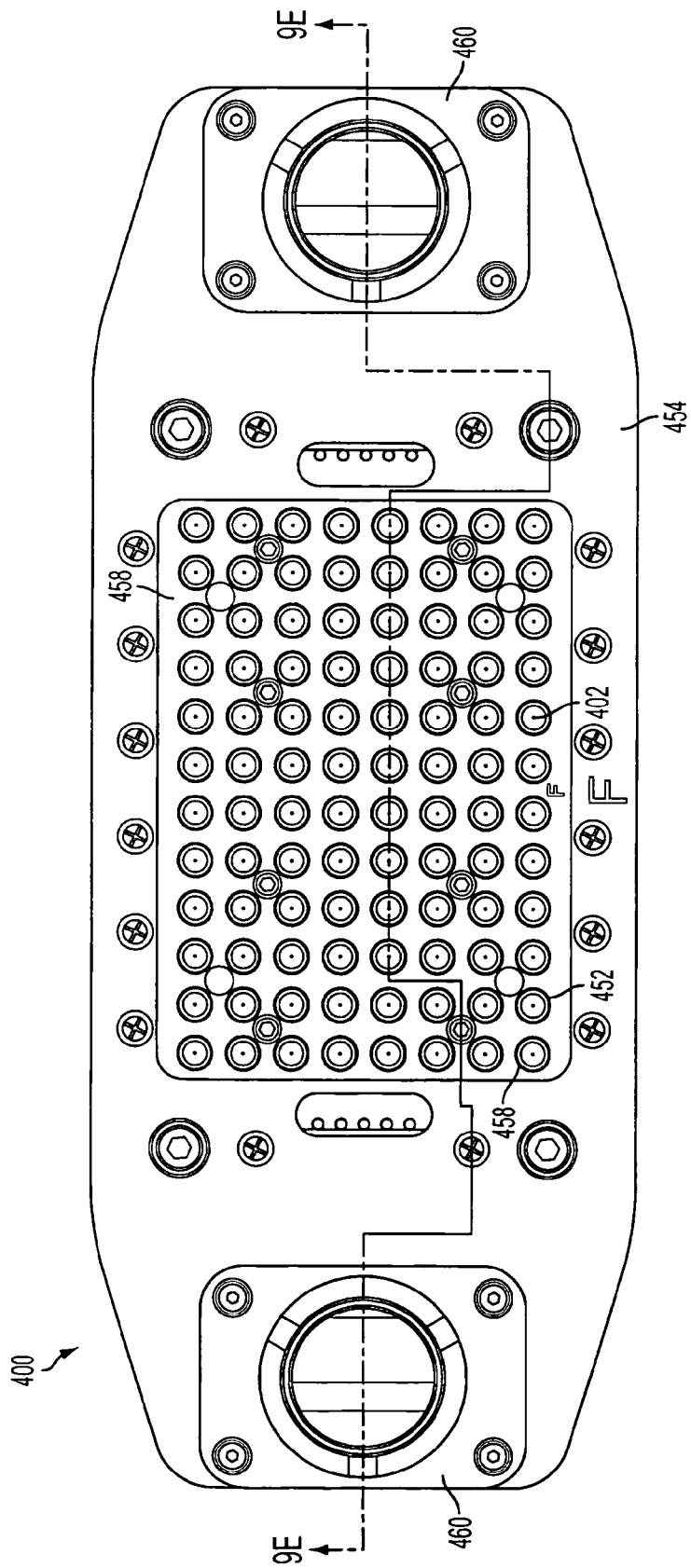
FIG. 9D is a top view of the electroporation tip manifold of FIG. 9A.
Figure 9E:
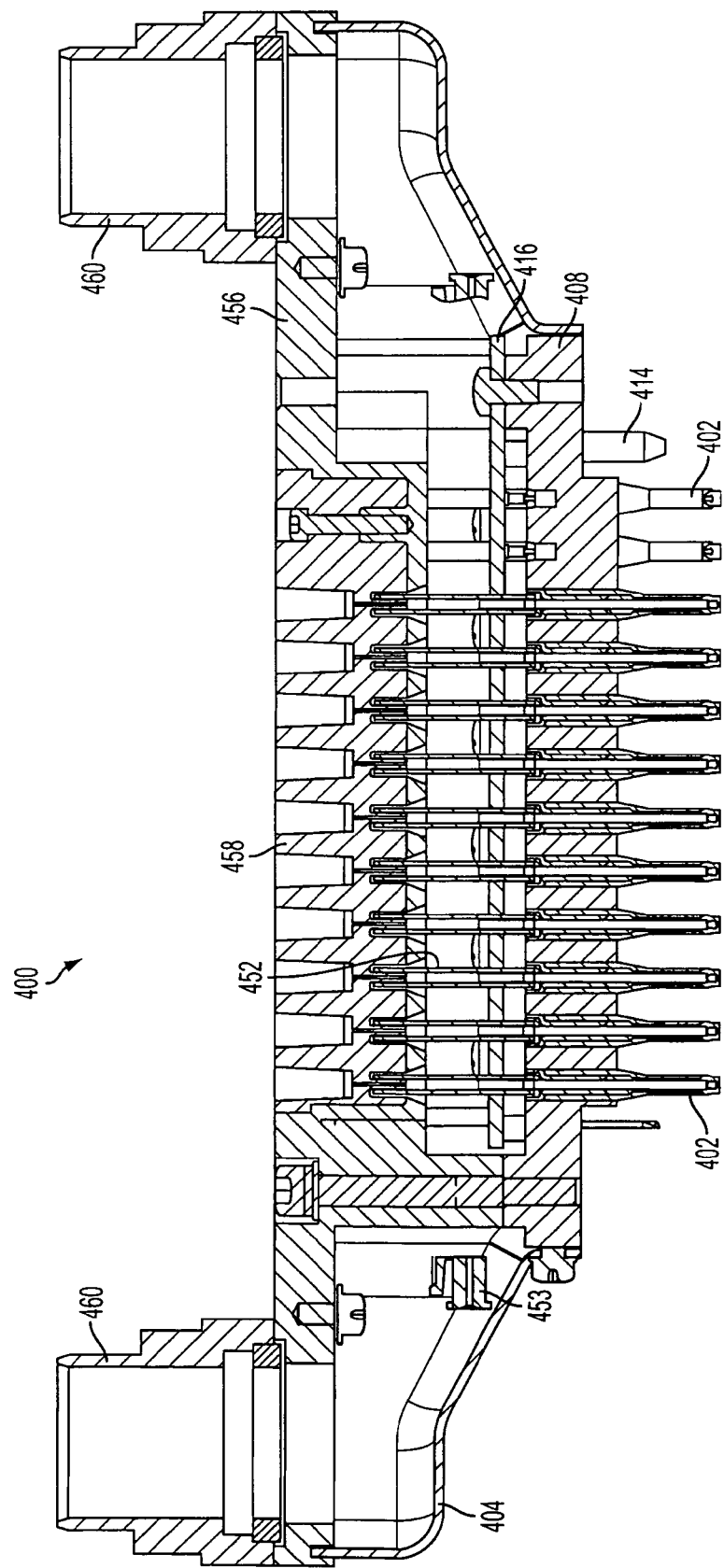
FIG. 9E is a cross-sectional view of the electroporation tip manifold of taken along line E-E of FIG. 9D.
Figure 9F:
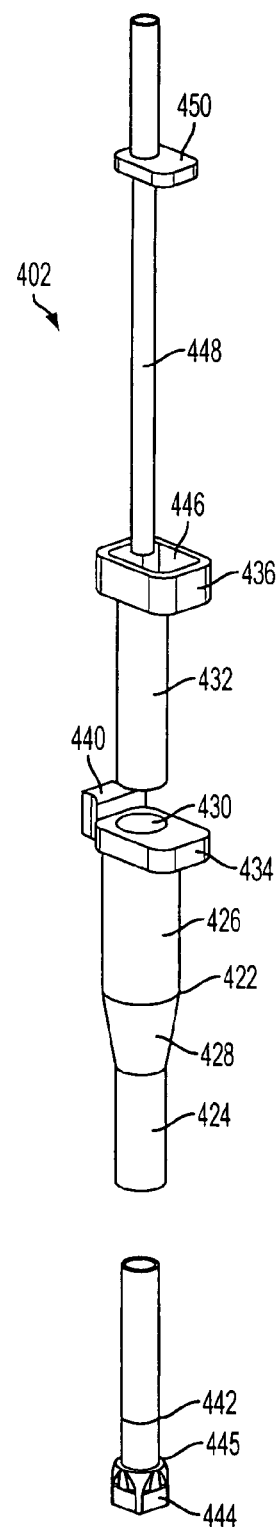
FIG. 9F is an exploded view of an electroporation tip assembly.
Figure 9G:
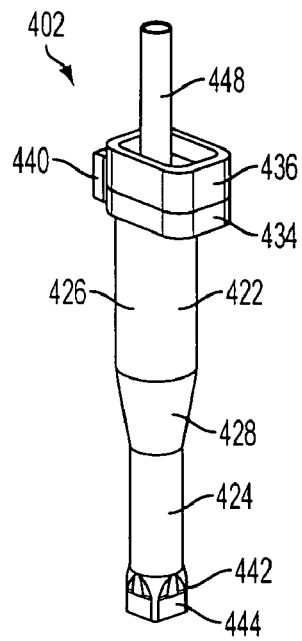
FIG. 9G is a perspective view of the electroporation tip assembly of FIG. 9F.
Figure 9H:
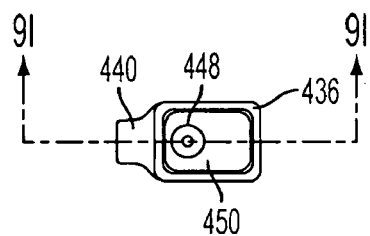
FIG. 9H is a top view of the electroporation tip assembly of FIG. 9F.
Figure 9I:
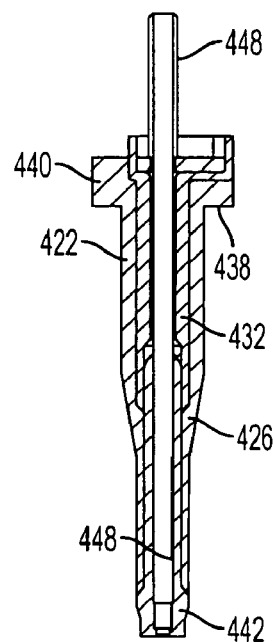
FIG. 9I is a cross-sectional view of the electroporation tip assembly taken along line I-I of FIG. 9H.

Referring to FIG. 9A, an exploded view of another electroporation tip manifold 400 including alignment pins and ninety-six, spring loaded electroporation tips is shown. For additional clarity, the following description also refers to FIGS. 9B-9E, which show front, side, top and cross-sectional views of the electroporation tip manifold 400. The manifold has ninety-six, spring loaded electroporation electroporation tip assembly 402 arranged in an 8×12 array. Again the spacing of the electroporation tip assembly 402 is double that of the wells. Accordingly, each well of a 348 well plate could be covered in four passes of the manifold 400. By having spring loaded electroporation tips, a 4th degree adjustment of the tips 402 occurs (namely adjustment along axis 116 with respect to FIG. 1).

The manifold 400 includes a cover 404 that forms an opening 406 for a tip guide plate 408. The tip guide plate 408 provides an aperture 410 for each electroporation tip assembly 402. The tip guide plate 408 retains two primary alignment pins 412 for aligning the multiwell plate to the electroporation tip assemblies 402. The tip guide plate 408 also retains optional secondary alignment pins 414 for shallowly engaging alignment holes on the multiwell plate for providing additional stability and positioning.

The tip guide plate 408 is aligned to an interconnection printed circuit board (pcb) 416 by dowel pins 418. The pcb 416 couples to each electroporation tip assembly 402 along with the tip guide plate 408 to provide electrical interconnection and mechanical spring loading to the electroporation tip assemblies 402. The pcb 416 has two-pronged pin assemblies 420 depending therefrom. The pcb 416 defines holes that retain a biasing element such as a spring (not shown) for providing downward force against the respective two-pronged pin assemblies 420.

Referring now to FIGS. 9F-9I, various view of an electroporation tip assembly 402 is shown. Each electroporation tip assembly 402 has an outer electrode 422 with a lower portion 424 that is relatively narrower than an upper portion 426. Intermediate the upper and lower portions 424, 426, the outer electrode 422 has a narrowing potion 428. The outer electrode 422 defines an interior 430 for receiving an electrode spacer 432 substantially in the upper portion 426. The outer electrode 422 and spacer 432 have complementary rectangular collars 434, 436, respectively, to establish the relationship there between. The outer electrode collar 434 also forms a banking surface 438, best seen in FIG. 9I, that prevents the electroporation tip assembly 402 from passing through the respective hole of the tip guide plate 408. Thus, the electroporation tip assembly 402 simply rests in the tip guide plate 408 and may move upward. There is also an outer electrode contact 440 adjacent the collar 434 on the outer electrode 422.

The lower portion 424 of the outer electrode 422 substantially houses a tip base 442. Both the spacer 432 and tip base 442 extend into the narrowing region 428 so that each is securely engaged to the outer electrode such as by an interference fit, welding, adhesive or the like. The tip base 442 has a distal portion 444 of a predetermined size so that when the distal portion 444 abuts the bottom of a well, the spacing between material in the bottom of the well and operative portions of the tip electrode is set. The distal portion 444 forms a shoulder 445 against which the lower portion 424 abuts. The spacer 432 also defines an interior 446 for receiving an inner electrode 448. The inner electrode 448 also has an inner electrode contact 450 that nestles within the spacer collar 436. As the inner electrode 448 extends deeply into the outer electrode interior 430, the inner electrode 448 may also be secured therein at the narrowing portion 428.

Referring again to FIGS. 9A-E, when assembled, the two-pronged pin assemblies 420 depending from the pcb 416 engage the electroporation electroporation tip assembly 402. In particular, one of the prongs is configured to make electrical contact with the outer electrode contact 440 while the other prong is configured to make electrical contact with the inner electrode contact 450 and, thereby, complete the electrical circuit through connectors 453. Additionally, as the two-pronged pin assemblies 420 is spring biased, if an upward force acts upon the electroporation electroporation tip assembly 402, the electroporation tip assembly 402 may move upward but contact is maintained.

Figure 9J:
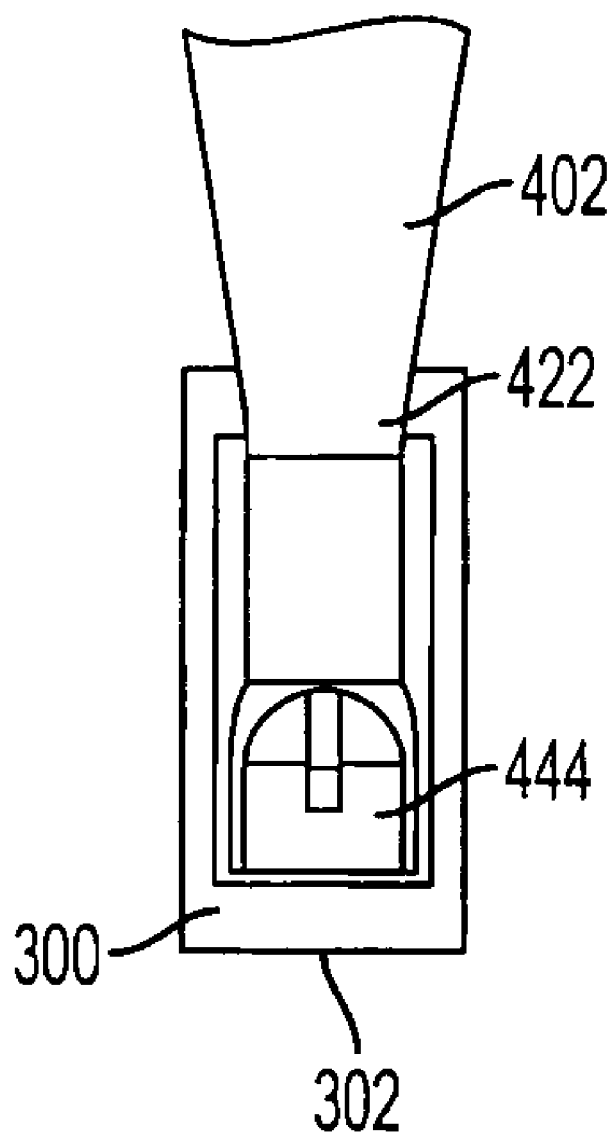
FIG. 9J illustrates the spring loaded tip of FIG. 9A inserted in a well of a multiwell plate.

For example, if a well plate had irregular well depth, the electroporation electroporation tip assembly 402 may be inserted beyond the depth. By virtue of allowing upward motion and having a spacer 442, each electroporation tip assembly 402 would be advantageously oriented the same distance from the bottom of the well. Referring to FIG. 9J, an exemplary electroporation tip assembly 402 is shown disposed in an exemplary well 302. The spring loaded electroporation electroporation tip assembly 402 is inserted in the well 302 of a multiwell plate 300. The electroporation tip assembly 402 may be adapted to perform aspiration and/or electroporation.

The electroporation tip assembly 402 is lowered into the respective wells 302 by movement of the robotic member 110 along axis 116 shown in FIG. 1. Preferably, each of the wells 302 has a substantially flat surface at the bottom of the well 302. The electroporation tip assembly 402 is lowered into each well 302 and beyond a point where the spacer 442 touches the bottom. As a result, the spring loading is utilized to set a predetermined distance between the bottom 360 of the respective well 302 and the operative portion of the electroporation tip assembly 402. In one embodiment, the predetermined distance is about 75 micrometers.

Preferably, an electroporation liquid is disposed in the well 302 and a biological material (e.g., cells) to be electroporated are disposed in the bottom of the well 302. The biological material may be a mammalian cell but can include other suitable substrates (e.g., lipid vesicles). The biological material may lie at or be adhered to the bottom of the well 302. The wells 302 defined in the multiwell plate body 304 are generally square shaped to complement the shape of the spacer 442.

Referring again to FIGS. 9A-9E, the manifold 400 also includes tubes 452 for establishing a fluid path between the electroporation tip assembly 402 and fluid connection plate assembly 454. The fluid connection plate assembly 454 has an outer frame 456 that supports a fluid distribution plate 458. Two carrier support assemblies 460 mount to the outer frame 456 of the fluid connection plate assembly 454 to allow coupling the manifold 400 to another component. A plurality of fasteners 462 and washers 464, only some of which are labeled for simplicity, secure the manifold components together.

Figure 10:
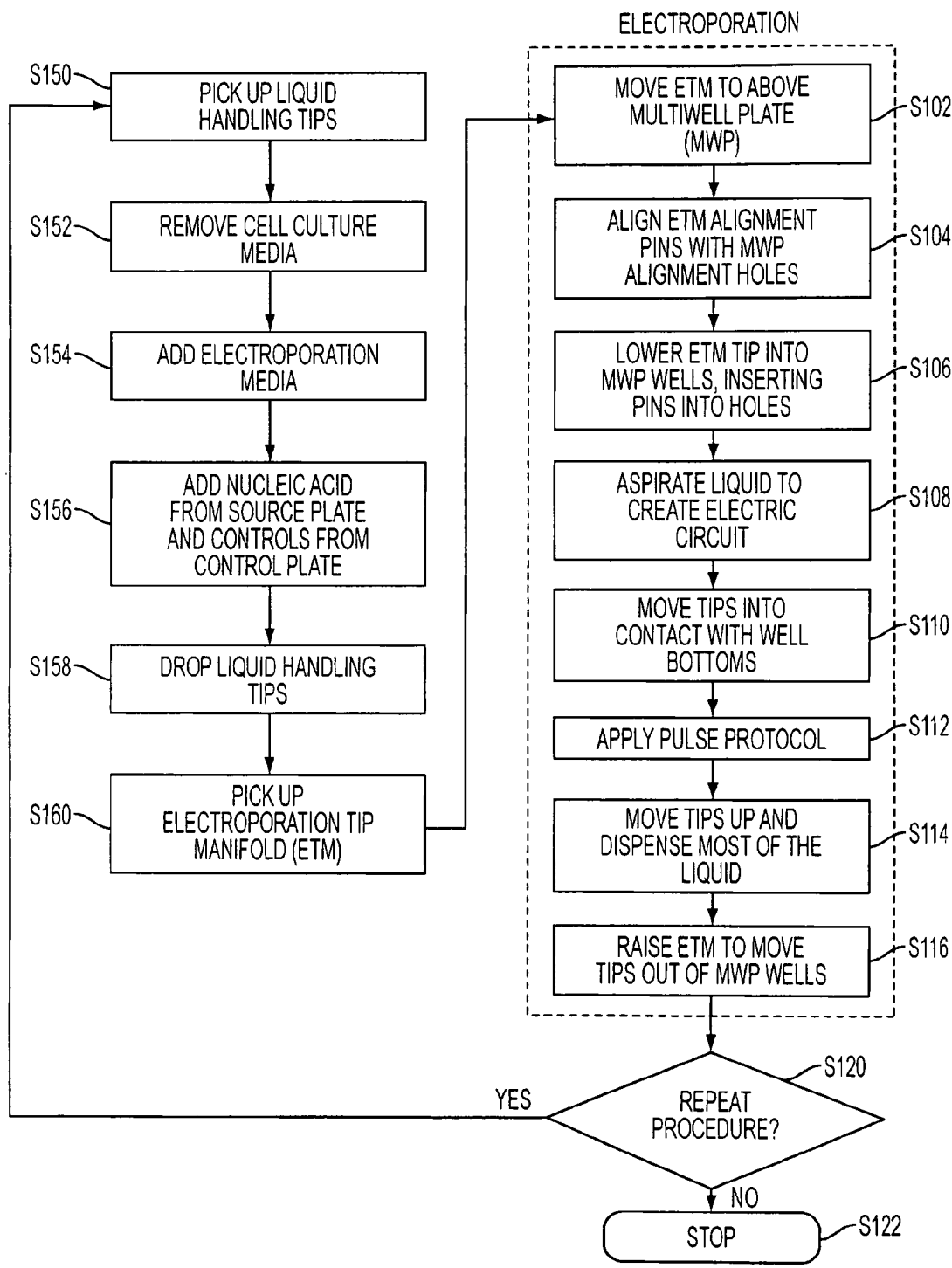
FIG. 10 is a flowchart related to a method of practicing an embodiment of the invention.

FIG. 10 illustrates a flowchart having the steps of a method of the invention. In particular, the flowchart illustrates electroporation with the electroporation steps S102-S-116 identified by being enclosed in a dotted line box. However, the method is not limited to electroporation procedures and can be used for other screening investigations. Before the electroporation procedure begins, steps S150-S160 may be performed to prepare the media in the tips 202.

Initially, the multiwell plate must be prepared. In step S150, the robotic member 110 can pick up liquid handling tips for withdrawing source liquids stored at the stations 132, 134, 136, 138, 140.

For illustration, FIG. 10 will be explained with respect to the transfection of HeLa cells with siRNA specific for polo-like kinase 1 (PLK1), where a successful transfection should result in a complete loss of viability compared to controls after 72 hours of incubation post transfection. First, 1000 HeLa-S3 cells (ATCC number CCL-2.2) are seeded in each well of the multiwell plate 300 in 40 µl volume of DMEM medium (available from Invitrogen of Carlsbad, Calif., as article number 32430-027) supplemented with 10% fetal bovine serum and 1% Penicilling/Streptomcyin. Once seeded, the multiwell plate 300 is incubated at 37° C. in 5% $CO_s$ for 24 hours.

After incubation, the multiwell plate 300 is ready for transfection. In step S152, the robotic member 110 is readied with appropriate liquid handling tips on a tip manifold. The cell culture medium is removed, typically leaving 10 µl of residual medium.

In step S154, the electroporation media is added to the wells 302. In step S156, a nucleic acid (e.g., siRNA specific for PLK1) from the source plate can be added along with the controls from the control plate. For example, siRNA and electroporation buffer are added. In one embodiment, the siRNA and electroporation buffer total an additional 27 µl, resulting in a total of 37 µl in each well 302. The robotic member 110 may move the liquid handling tips to a wash station for cleaning intermediate the steps S154, S156. In step S158, the robotic member 110 drops the liquid handling tips to ready for coupling to an electroporation tip manifold (ETM) 200.

In step S160, the ETM 200 is picked up by the robotic member 110 to be ready to start the electroporation procedure. In step S102, the robotic member 110 moves the ETM 200 to a position above the multiwell plate (MWP) 300 disposed on the table 120. At completion of step S102, the ETM 200 is approximately aligned above the MWP 300 in preparation for precise alignment in the upcoming steps. In step 8104, the ETM pins 210, 212 may be more precisely aligned with MWP alignment holes 310a, 312a.

In step S106, the ETM pins 210, 212 are inserted into the alignment holes 310a, 312a so that the MWP 300 precisely aligns with the ETM 200 as described above.

In step S108, the liquid is aspirated to create an electric current or circuit. For example, the tips 202 withdraw a total of 15 µl of liquid, leaving 22 µl in the respective well 302. Then, the tips 202 are lowered in to the wells 302, stopping 2 mm above the well bottom 360. By having the 15 µl of liquid aspirated into the tips 202, electrical contact between the inner and outer electrode of each of the electroporation tips is created, e.g., the tip electrical circuit is closed. The electrodes of the tips 202 are connected to a square wave pulse generator (not shown) that can deliver high voltage pulses to the tips.

In step S110, the tips 202 are moved into contact with the respective well bottoms 360. Preferably, the tips 202 are spring loaded as described above. In step S112, a pulse protocol is applied. The pulse protocol can vary widely depending on the cell type. For PLK1, a suitable pulse protocol is 25 pulses with 25 ms pulse length at 0.1 second intervals with 130 V applied.

In step S114, the tips 202 may be moved up above the bottom surface 360 of the well 302 to dispense most of the liquid. Alternatively, the tips 202 may proceed directly to a wash station where the liquid is dispensed to waste.

In step S116, the ETM tips 202 are moved out of the MWP wells 302. The electroporation procedure may be repeated S120 to cover another portion of the wells with the tips, or stopped at step S122 and incubation occurs. In the 384 wells 302 and 48 tip 202 embodiment, the process steps S106-S116 would occur seven more times for alignment hole pairs 310b-h, 312b-h, to perform the electroporation procedure on all 384 wells 302. It is further possible to wash and replace the tips and collect new biological material during the process such that portions of the wells include different screening materials.

Once the electroporation protocol is complete the electroporated cells may be cultured in the presence of the transfected molecule. For example, after electroporation in the PLK-1 assay 28 µl of medium is added. The additional medium is supplemented with 15% fetal bovine serum and 1.5% Penicillin/Streptomycin, resulting in 50 µl final volume with 10% fetal bovine serum and 1% Penicillin/Streptomycin which is then incubated at 37° C. in 5% $CO_s$ for 72 hours.

After incubation, the transfection efficiency and viability can be evaluated. The system 100 can facilitate the evaluation or the evaluation can be performed outside the system. For the PLK1 example, the system can remove some of the medium from the MWP 300. By using a liquid handling manifold (not shown) coupled to the robotic member 110, the system 100 can then add 40 µl 10% Alamar Blue reagent in DMEM medium supplemented with 2% fetal bovine serum. After incubation for 2 hours at room temperature, protected from light, the transfection efficiency and viability is evaluated using a SAFIRE²™ plate reader available from Tecan Trading Group AG in Lausanne, Switzerland according to the manufacturer's instructions.

Figure 11:
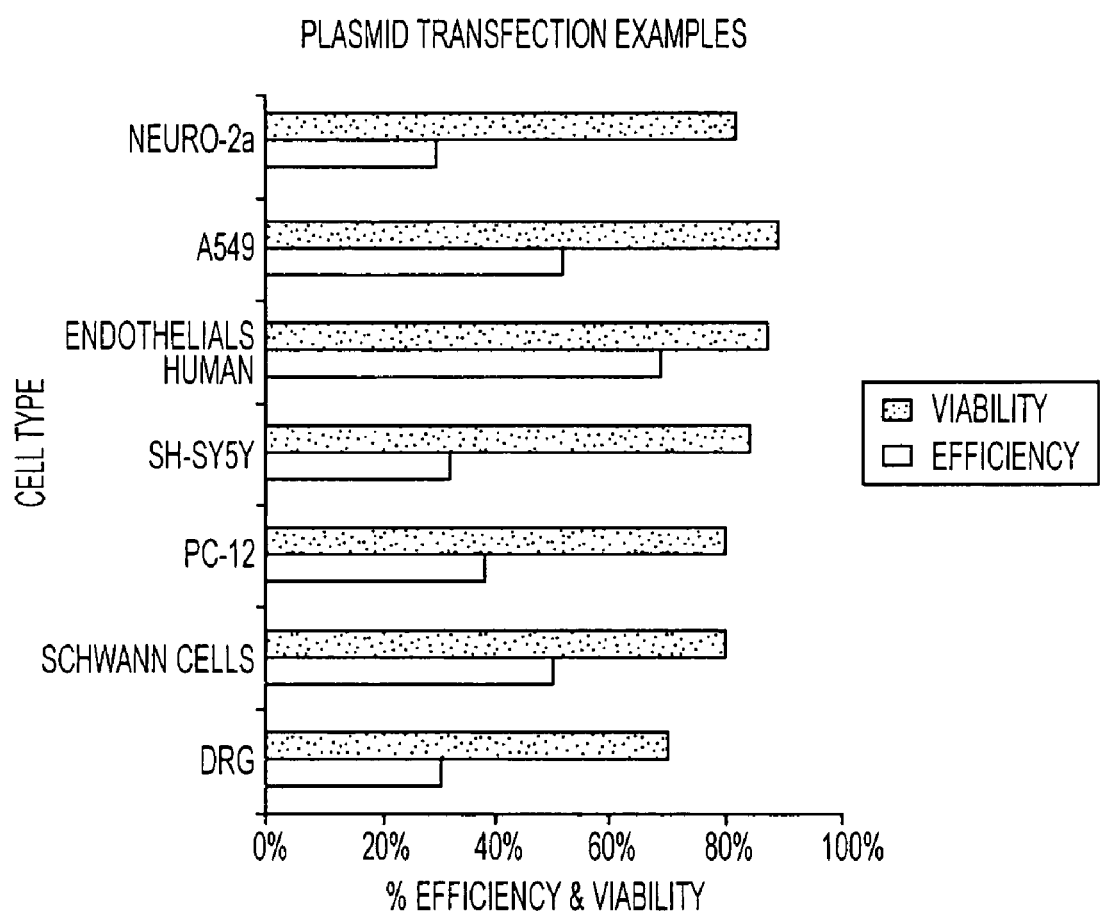
FIG. 11 shows results from a plasmid transfection assay using the subject technology.
Figure 12:
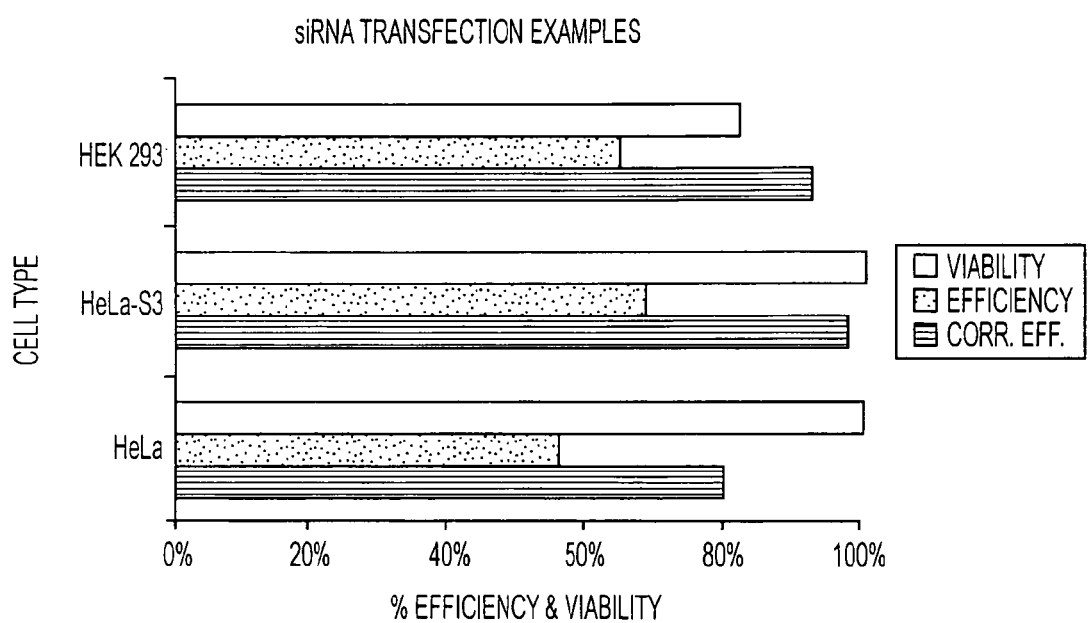
FIG. 12 shows results from a siRNA transfection assay in accordance with the instant disclosure.

FIGS. 11 and 12 show results of automatic screening using the apparatuses and methods of the invention. FIG. 11 shows viability and efficiency results from a plasmid transfection. The percentages of efficiency and viability are shown for cell types DRG, Schwann cells, PC-12, SH-SY5Y, Endotheliasis (human), A549, and Neuro-2a. FIG. 12 shows percentages of viability and efficiency of a siRNA transfection of HeLa, HeLa-S3, and HEK 293 cell types.

One advantage of the subject technology is that it provides an electroporation tip manifold equipped with alignment pins offering high precision in placement.

Another advantage of the subject technology is that it provides an electroporation tip manifold and multiwell plate alignment apparatus and method in which the tips can be aligned, lowered, and placed in close proximity to the surface of a cell culture well. During electroporation, the electric field can then be focused between the bottom of the well and the tip capillary electrode, thereby creating a virtual electroporation cuvette. In this way, the cells are electroporated directly in their inherent state, with improved viabilities.

Another advantage is that the alignment apparatus and method facilitates high screening throughput. It is scalable to handle a high number of investigations to enable applications such as genome-wide RNAi screening on biologically relevant cell types. Other high throughput/high scale applications include cDNA screening, intracellular target characterization, biological systems interrogations of signalling pathways and administration of intracellular drugs. Furthermore, the apparatuses of the various embodiments of the invention can be relatively easy and inexpensive to manufacture.

It is to be understood that both the foregoing general description and the following description are exemplary and are intended to provide further explanation of the invention claimed.

The accompanying figures, which are incorporated in and constitute part of this specification, are included to illustrate and provide a further understanding of the apparatus and method of the invention. Together with the description, the drawings serve to explain the principles of the invention.

All statements herein reciting principles, aspects, and embodiments of the invention, as well as specific examples thereof, are intended to encompass both structural and functional equivalent thereof. Additionally, it is intended that such equivalents include both currently known equivalents as well as equivalents developed in the future, i.e., any elements developed that perform the same functions, regardless of structure.

Although the foregoing invention has been described in some detail by way of illustration and examples for purposes of clarity and understanding, it will be apparent to those skilled in the art that certain changes and modifications can be practiced. Therefore, the description and examples should not be construed as limiting the scope of the invention, which is delineated by the appended numbered claims.

What is claimed is:

1. An apparatus for screening of biological material comprising:
   a multiwell plate comprising a plurality of wells for holding biological material and a first alignment hole;
   a table for supporting the multiwell plate;
   a tip manifold having a plurality of tips and an alignment pin, the alignment pin being relatively longer than the tips; and
   a robotic member for moving the tip manifold so that a plurality of alignment pin inserts in the alignment hole to align the tips of the tip manifold to at least some of the wells of the multiwell plate.

2. The apparatus of claim 1 wherein the tip manifold comprises a second alignment pin, and the multiwell plate has a second alignment hole so that when the alignment pins insert in the alignment holes, a rotational alignment of the multiwell plate is set.

3. An apparatus for use during screening of biological material comprising:
   a tip manifold comprising:
      (i) a plate;
      (ii) at least one tip depending from the plate;
      (ii) a first tip alignment pin depending from the plate; and
      (iii) a second tip alignment pin depending from the plate, the second tip alignment pin opposing the first tip alignment pin; and
   a multiwell plate comprising:
      i) a plurality of wells for holding biological material;
      (ii) a first alignment hole; and
      (iii) a second alignment hole, the second alignment hole opposing the first alignment hole; wherein each of the wells has a substantially flat bottom, and the at least one tip is spring-biased and lowered to contact the flat bottom.

4. A method of aligning a plurality of tips of a tip manifold with a plurality of wells of a multiwell plate comprising the steps of:
   providing at least two alignment holes, at least one of the alignment holes formed on a first side of the multiwell plate, and at least one of the alignment holes formed on a second side of the multiwell plate;

providing at least two alignment pins, at least one of the alignment pins coupled to a first side of the tip manifold, and at least one of the alignment pins coupled to a second side of the tip manifold;

inserting the at least two alignment pins into at least two alignment holes to align the multiwell plate to the tip manifold; and guiding the plurality of tips into a plurality of wells after the insertion of the at least two alignment pins.

5. The method of claim 4 wherein the at least one tip is an electroporation tip.

6. The method of claim 4 wherein a number of wells is at least two times a number of tips, the multiwell plate has third and fourth alignment holes, and further comprising the step of:

inserting the at least two alignment pins into the third and fourth alignment holes to realign the multiwell plate to the tip manifold; and guiding the plurality of tips into a second plurality of wells after the reinsertion of the at least two alignment pins.

* * * * *